United States Patent [19]
Eydelman et al.

[11] Patent Number: 5,583,438
[45] Date of Patent: *Dec. 10, 1996

[54] INDUCTIVELY COUPLED DEDICATED RF COILS FOR MRI

[75] Inventors: Gregory I. Eydelman, West Hempstead; Anthony Giambalvo, Kings Park; Raymond V. Damadian, Woodbury, all of N.Y.

[73] Assignee: Fonar Corporation, Melville, N.Y.

[*] Notice: The portion of the term of this patent subsequent to Oct. 16, 2013, has been disclaimed.

[21] Appl. No.: 728,541

[22] Filed: Jul. 11, 1991

Related U.S. Application Data

[63] Continuation-in-part of Ser. No. 337,041, Apr. 12, 1989, Pat. No. 5,050,605.

[51] Int. Cl.$^6$ ................ G01V 3/00; G01V 3/14; A61B 5/055
[52] U.S. Cl. ............... 324/318; 324/322; 128/653.5
[58] Field of Search ................... 324/300, 307, 324/309, 318, 322; 128/653.5

[56] References Cited

U.S. PATENT DOCUMENTS

| | | | |
|---|---|---|---|
| 4,742,304 | 5/1988 | Schall et al. | 324/322 X |
| 5,003,265 | 3/1991 | Leussler | 324/318 |
| 5,050,605 | 9/1991 | Eydelman et al. | 324/318 X |
| 5,243,289 | 9/1993 | Blum et al. | 324/322 |

OTHER PUBLICATIONS

"Electrical Fundamentals for Technicians", Second Edition, Shrader, pp. 128–130, 408–411 (1977).

"The Performance of Mutually–coupled Coils for Magnetic Resonance Signal Recovery", Gilderdale, et al., Society of Magnetic Resonance in Medicine, Book of Abstracts, vol. 2, p. 256 (1989).

"Inductive (Flux Linkage) Coupling to Local Coils in Magnetic Resonance Imaging and Spectroscopy", Froncisz et al., Journal of Magnetic Resonance, vol. 66, pp. 135–143 (1986).

"Dedicated Coils in Magnetic Resonance Imaging", Sobel, Reviews of Magnetic Resonance in Medicine, vol. 1, No. 2, pp. 181–224 (1986).

"Optimization of Receiver Coil Bandwidth by Inductive Coupling", Darrasse, et al., Society of Magnetic Resonance in Medicine, Works in Progress, p. 1340 (1990).

"Optimized RF Coils for Low Field MRI", Leussler, et al., Society of Magnetic Resonance in Medicine, Book of Abstracts, vol. 2, p. 938 (1989).

"Estimation of the SNR Loss Due to Inductive Coupling Loops", Wright, Society of Magnetic Resonance in Medicine, Book of Abstracts, vol. 2, p. 955 (1989).

*Primary Examiner*—Sandra L. O'Shea
*Assistant Examiner*—Mack Haynes
*Attorney, Agent, or Firm*—Brooks Haidt Haffner & Delahunty

[57] ABSTRACT

A primary tuned circuit and a secondary tuned circuit are inductively coupled. Primary and secondary inductors of the tuned circuits each exhibit a respective region of sufficiently uniform sensitivity for MRI studies. Both the primary and secondary inductors receive, in use, an MRI signal directly from a subject to be imaged.

50 Claims, 3 Drawing Sheets

INDUCTIVELY COUPLED DEDICATED RF COILS FOR MRI

CROSS REFERENCE TO RELATED APPLICATION

The present application is a continuation-in-part application of prior application Ser. No. 07/337,041, filed on Apr. 12, 1989 now U.S. Pat. No. 5,050,605, entitled Magnetic Resonance Imaging Antennas with Spiral Coil and Imaging Method Employing the Same, and commonly assigned herewith.

BACKGROUND OF THE INVENTION

The present invention relates to dedicated radio frequency coils for use in magnetic resonance imaging (MRI) of biological subject, and more particularly tuned inductively coupled coils of this type.

The development of dedicated radio frequency (RF) coils has long been a topic of interest in the MRI field. A useful introduction to the subject can be found in the article by W. T. Sobel, "Dedicated Coils in Magnetic Resonance Imaging," Reviews of Magnetic Resonance in Medicine, Vol. 1, No. 2, pp. 181–224 (1986). In his paper, Sobel distinguishes between magnetic resonance imaging (MRI) and magnetic resonance spectroscopy (MRS). The same distinction is made in the present specification, in which references to imaging refer to two-dimensional Fourier transform imaging (which may be derived from spectral information) as opposed to spectroscopy which involves the reproduction of a nuclear magnetic resonance spectrum.

Several RF coil features and parameters directly affect its suitability for use in magnetic resonance imaging. Ideally, the coil would have a high uniform sensitivity within a particular spatial region of interest, and low sensitivity elsewhere, with a resulting high signal-to-noise (SNR) ratio. The coil would be large enough to achieve the spatial coverage desired, but small to achieve a high fill factor, to fit within the MRI system magnet and to conform comfortably to the body of a subject. The RF coil must resonate at approximately the Larmor frequency of the nuclei used to develop the MRI signal, so that neither the coil size nor geometry can create an inductance or self-capacitance which prevents tuning to the desired frequency. The coil must also couple to the MRI system amplifier stage efficiently.

One technique for coupling the RF coil to the imaging system amplifier stage is inductive coupling. In this scheme, a primary winding is positioned proximate the part of the subject which is to be imaged and a second winding, typically a single loop, is positioned adjacent the primary winding for inductively coupling with it. The secondary loop is coupled to the MRI system amplifier. Magnetic resonance signals are excited within the subject under magnetic field conditions to permit imaging and are received by the primary winding. Current flowing in the primary winding induces a voltage in the secondary winding which is amplified and processed to develop an image.

At this juncture, there is no comprehensive analysis of inductively coupled RF coils for MRI. The importance of the degree of inductive coupling between the primary and secondary coils, their relative spatial positions and respective geometries, and how these factors fit into the other aspects of RF coil design mentioned above, remain largely unanswered. The various inductively coupled RF coils analyzed in the literature appear to be special cases of the general problem.

The article by W. Froncisz et.al., "Inductive (Flux Linkage) Coupling to Local Coils in Magnetic Resonance Imaging and Spectroscopy," Journal of Magnetic Resonance 66, pp. 135–143 (1986), presents an analysis of an inductively coupled coil for use in MRI. The secondary coil is an untuned single loop and its sole purpose is to couple the primary coil to a receiver. The article concludes, among other things, that detuning can be minimized by making the secondary coil with the smallest possible inductance and coupled as tightly as possible to the primary coil.

A loop array structure was proposed by C. Leussler et.al. "Optimized RF Coils for Low Field MRI," Proc. SMRM 1989, p. 938, for applications where solenoids previously had found use. They disclose a head coil comprised of eleven turns and a body coil of eight turns, wherein each turn is a single loop LC resonator. Each resonator is tuned to the same frequency. The article presents data to show that the Q of the loop array is degraded less than the Q of the solenoid when loaded, over a frequency range of about 2.5 to 25 MHz.

Signal-to-noise ratio was considered in the article of D. J. Gilderdale et.al. in "The Performance of Mutually-Coupled Coils for Magnetic Resonance Signal Recovery," Proc. SMRM, p. 956 (1989). The authors concluded that in an inductively coupled coil system, the best SNR is obtained when the primary and secondary coils are slightly overcoupled and the lower frequency peak of the coil system frequency response is tuned to the frequency of interest.

The SNR of inductively coupled systems in which the secondary coil is significantly larger than the primary coil was investigated in the paper by S. N. Wright, "Estimation of the SNR Loss Due To Inductive Coupling Loops," Proc. SMRM, p. 955 (1989). The paper concludes that there will be less than a five percent drop in SNR of the coupled system relative to the primary alone, if the input resistance of the system is greater than ten times the primary coil resistance.

Finally, L. Darrasse et.al., "Optimization of Receiver Coil Bandwidth by Inductive Coupling," Proc. SMRM, p. 1340 (1990) discloses a strongly overcoupled inductively coupled coil having a large bandwidth for fast scanning on a low field MRI system.

Significantly, the prior art largely relies on an analysis of inductively coupled coils which is based on a lumped parameter circuit model. There is little, if any, consideration of the spatial sensitivity distribution of the primary coil, and usually there is a tacit assumption that the NMR signal is received by only the primary coil, and then inductively coupled to the secondary coil. Additionally, signal-to-noise ratio is evaluated in terms of the NMR signal voltage and the noise voltage which is output from the secondary coil; not the SNR of the image which is ultimately formed. However, the spatial sensitivity of the coil system can play a determinative role in the image SNR that is achieved.

SUMMARY OF THE INVENTION

It is an object of the invention to provide a dedicated inductively coupled RF coil for magnetic resonance imaging which achieves good signal-to-noise ratio in the resulting image over a desired field of view.

Another object of the invention is to provide a dedicated inductively coupled RF coil which can easily be resonated at the hydrogen Larmor frequency for mid-range magnetic field strengths.

Another object of the invention is to provide a dedicated inductively coupled RF coil for MRI which can be conveniently configured for a particular anatomical study of humans without substantially sacrificing image signal-to-noise ratio, field of view, and the ability to resonate at the hydrogen Larmor frequency for mid-range magnetic field strengths.

According to the invention, a dedicated radio frequency coil for MRI is comprised of a tuned primary circuit and a tuned secondary circuit. Each of the tuned circuits is comprised of a capacitor and an inductor connected in series. The primary and secondary inductors are each dimensioned and shaped for defining a spatial region in which the coil sensitivity is sufficiently uniform for the MRI study which it is used to carry out. The primary and secondary inductors are positioned for inductively coupling the primary and secondary tuned circuits, and a port is provided for transferring radio frequency energy between the tuned secondary circuit and an external device.

The primary and secondary inductors are dimensioned and shaped for defining respective spatial regions of sufficiently uniform sensitivity which have a substantial non-overlapping portion so as to expand the resulting useful field of view relative to a single inductor.

The primary circuit inductor may comprise a spiral coil wound around an axis and extending progressively radially outward from the axis, or a plurality of such spiral coils wound around the axis and extending progressively radially outward therefrom, and means electrically connecting the spiral coils in parallel. Alternatively, the primary coil can be solenoidal.

The secondary circuit conductor can be solenoidal, a pair of loops connected in parallel, or simply a single loop tuned by a capacitor.

BRIEF DESCRIPTION OF THE DRAWINGS

The invention will be readily understood from the detailed description and the accompanying drawings in which.

DETAILED DESCRIPTION OF THE PREFERRED EMBODIMENTS

Figure 1:
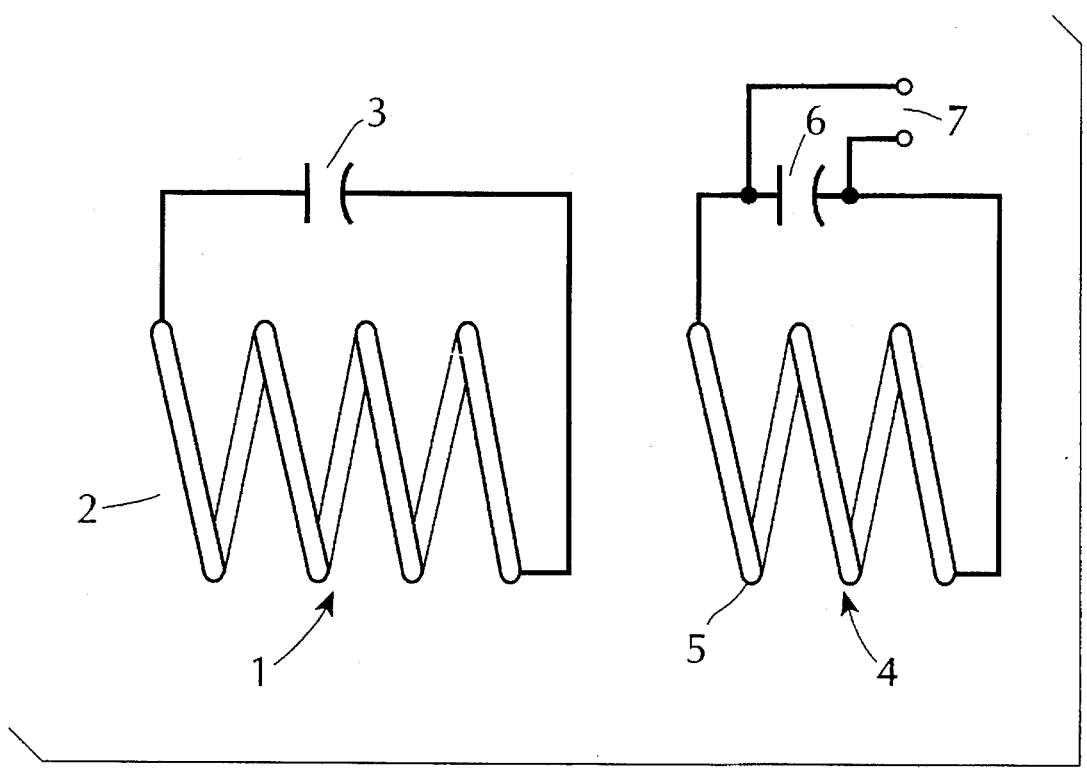
FIG. 1 is a side view of a first embodiment of the inductively coupled dedicated RF coil for MRI according to the invention.

FIG. 1 shows a first embodiment of the invention which is comprised of a tuned primary circuit 1 and a tuned secondary circuit 4. The tuned primary circuit is comprised of a primary inductor 2 and a primary circuit capacitor 3 connected in series with the inductor 2. The secondary circuit 4 is similarly comprised of the secondary inductor 5 and the secondary circuit capacitor 6 which is connected in series with the secondary inductor 5. A port 7, shown in the form of a pair of terminals, allows the transfer of radio frequency energy between the tuned secondary circuit and an external device.

The primary inductor 2 and the secondary inductor 5 are positioned sufficiently close and oriented so that the tuned primary and secondary circuits are inductively coupled. When part of a subject being studied is caused to emit MRI signals, the MRI signals induce a voltage in the primary inductor 2 which causes a current to flow through the primary circuit 1. This current generates a magnetic field which in turn induces a current in the tuned secondary circuit 4, because of the inductive coupling between the primary and the secondary circuits. The induced secondary circuit signal can be read, for example, as the voltage across the secondary circuit capacitor 6 through the port 7.

An important feature of the invention is that the secondary circuit inductor 5 is shaped and positioned to receive an MRI signal directly from the subject being studied. Thus, the RF energy within the secondary circuit is derived not only from energy coupled from the primary circuit, but the energy within the secondary circuit is also received directly from the subject.

Both the primary circuit 1 and the secondary circuit 4 are nominally tuned to the frequency of the NMR signal sought to be received. The degree of coupling between the primary inductor 2 and the secondary inductor 5 can be characterized as tight and approximately critical coupling. The primary and secondary inductors are not allowed to be overcoupled to a degree where multiple resonances occur in the frequency response characteristic of the coil system. Because, in the present invention, the secondary inductor is used for directly receiving an appreciable amount of energy from the subject being studied, coils according to the invention appear to be somewhat less sensitive to the degree of inductive coupling than those conventional coils in which the coupling loop is used simply for transferring energy from the primary coil to the MRI system receiver. Final tuning of the coil is achieved in the conventional manner by the MRI system receiver which typically includes a variable capacitance element and which carries out final tuning after the subject has been inserted in the coil.

Figure 2:
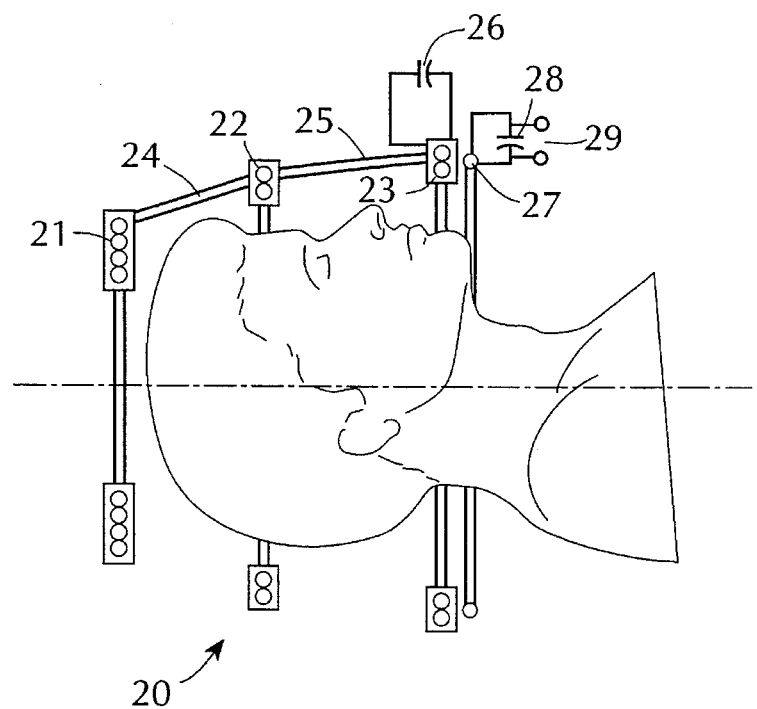
FIGS. 2 and 3 are sectional views of second and third embodiments of the RF coil for MRI according to the invention.

The preferred embodiment shown in FIG. 2 has been found particularly effective for imaging the human head and the human knee. In the particular illustrated embodiment, the primary inductor 20 is comprised of three spiral coil sections: 21, 22 and 23. Each spiral coil section is wound around an axis and extends progressively radially outwardly from the axis. The axis is shown as a broken line in the drawing. The spiral coil sections 21, 22, and 23 are wound with a central opening so that a part of the subject, e.g. the head, can be inserted within the primary inductor 20.

The primary inductor further comprises conductors 24, 25. Each of the conductors 24, 25 is a pair of links for connecting the spiral coils electrically in parallel. A capacitor 26 is connected across the primary inductor 20 so as to form a tuned resonant primary circuit. The structure of the spiral windings and RF coils made from them is disclosed in related application Ser. No. 07/337,041, now U.S. Pat. No. 5,050,605, and commonly assigned herewith.

The coil shown in FIG. 2 further comprises a secondary circuit having an inductor 27 and a capacitor 28. The secondary inductor 28 to form a tuned resonant secondary circuit. The port 29 allows RF energy to be transferred between the tuned secondary circuit and an external device.

The secondary inductor 27 is positioned next to the winding 23 of the primary inductor 20. In addition, the secondary inductor 27 receives an NMR signal directly from the subject so that the coil sensitivity falls off less rapidly beyond the spiral winding 23 than is the secondary inductor 27 were not present.

Figure 3:
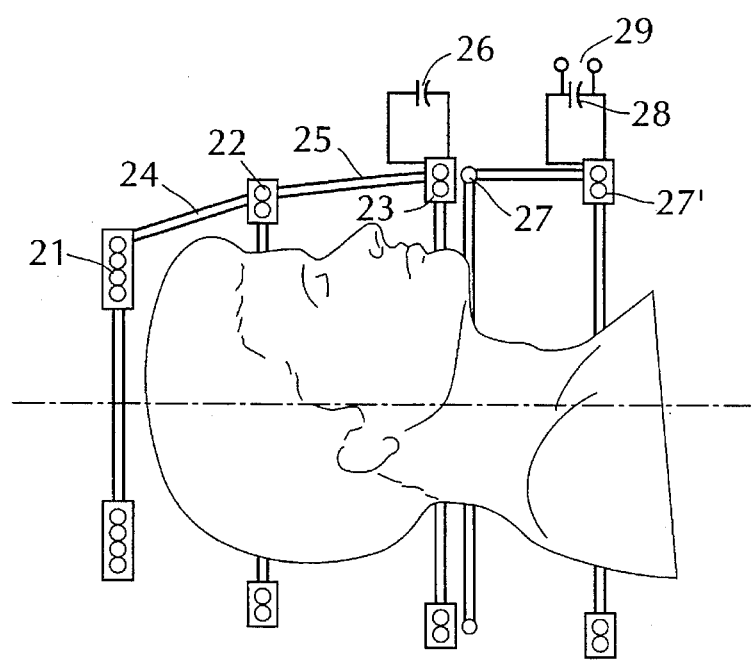

FIG. 3 illustrates an embodiment similar to that of FIG. 2, in which the secondary inductor has an increased axial extent. The secondary inductor is comprised of a first loop 27 and a second loop 27' which are electrically connected in parallel and tuned by a capacitor 28. The effect of the axial extension of the secondary inductor is to further extend the sensitive region of the coil within which images can be made.

EXAMPLES

The embodiment of the invention shown in FIG. 2 was made and tested. All coils and connecting links were made of copper tubing having a 0.25 inch outer diameter. Using the reference numerals in the drawing, coil 21 was a four turn circular spiral having an inner opening of about 5.5 inch diameter, coil 22 was a two turn oval having an inner opening of about 8.0 by 9.0 inches, coil 23 was a two turn oval having an inner opening of about 8.5 by 9.5 inches, and secondary inductor 27 was a single turn oval loop of about 9.0 by 10.0 inches. The center-to-center turn spacing within the spiral coils was about 5/16 inches, and the spacing between spiral coil 23 and secondary loop 27 was about 1/8 inch. The spacing between spiral coils 21 and 22 was about 2.5 inches, and between spiral coils 22 and 23 was about 3.0 inches. Tuning capacitors in the range of about 70 pf to 140 pf for the primary inductor and 10 pf to 30 pf for the secondary inductor allowed the inductively coupled coil according to the invention to be resonated in the 12 MHz region corresponding to a magnetic field strength of around 3000 gauss for hydrogen.

The embodiment shown in FIG. 3 was made having the same dimensions just described and with the secondary loop 27' spaced from secondary loop 27 by about 2.5 inches. Both embodiments were used on a clinical MRI scanner system without any modification to the system being required.

Figure 4:
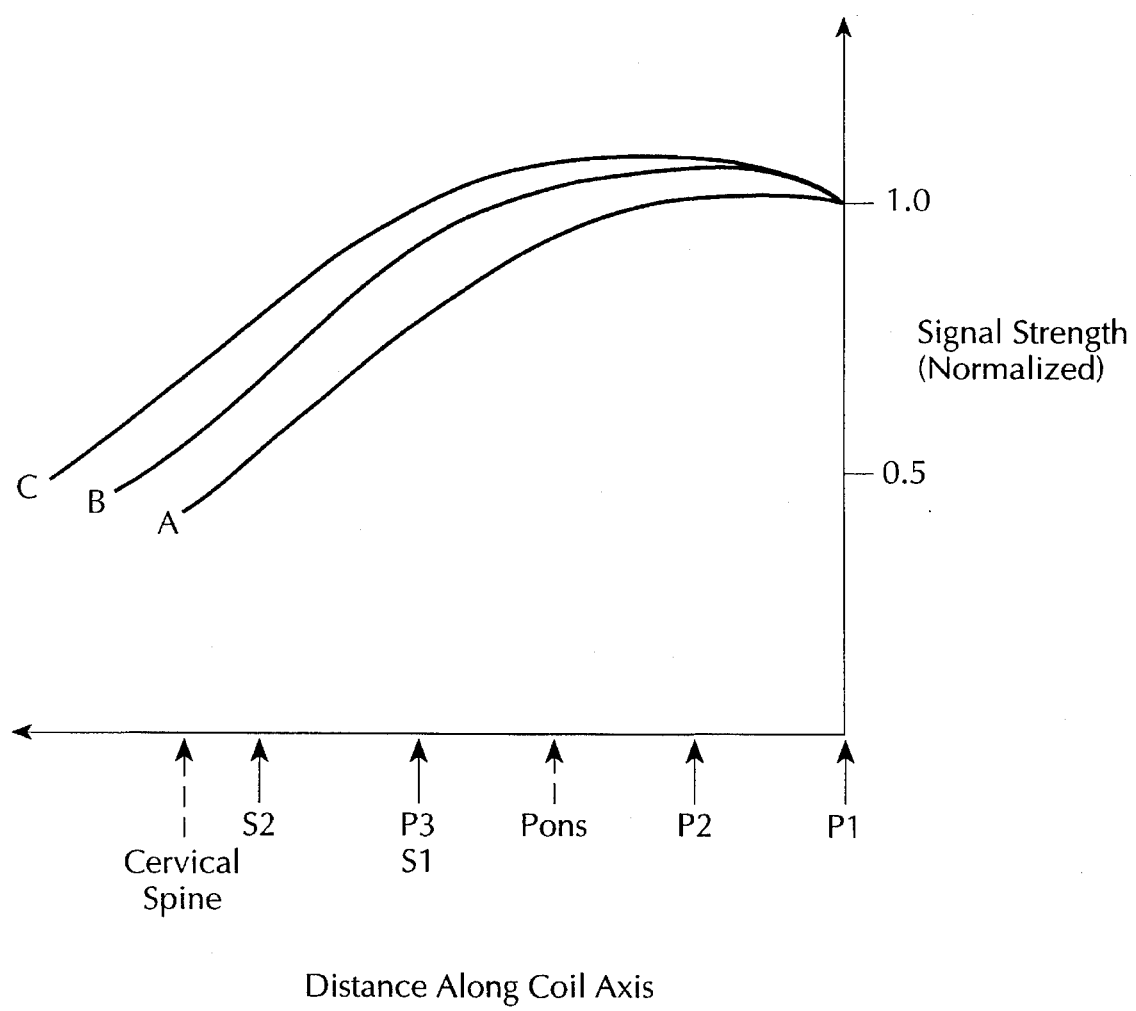
FIG. 4 is a graph illustrating the relative spatial sensitivity of the dedicated RF coil for MRI according to the invention and a known dedicated RF coil.

The performance improvement achieved by the coil according to the invention described in the preceding examples is shown in FIG. 4. The horizontal axis represents distance along the axis of the coil, and the vertical axis represents normalized signal strength which is achieved within the sensitive region of the coil. The positions P1, P2 and P3 on the distance axis mark the positions of the spiral coils of the primary inductor, and the positions S1 and S2 are the positions of the secondary inductor turns. Also shown are the positions of the pons region of the brain and the cervical spine of a typical human when positioned with his head inserted in the coil.

Curve A is the signal strength curve for the primary inductor alone, i.e. for the coil configuration disclosed in the prior copending application. Curve B shows the signal strength for the embodiment of the invention shown in FIG. 2. In the region beyond position P3, the signal strength remains high a further distance from the primary coil than in the case of Curve A. Curve C is the signal strength for the embodiment shown in FIG. 3 and shows a high signal strength at distances markedly greater from P3 than in the case of Curve B. In fact, the sensitive region of the embodiment of FIG. 3 is sufficient to permit high quality imaging of the cervical spine as well as the brain in humans.

What is claimed is:

1. A dedicated radio frequency coil for receiving MRI signals emitted from an anatomical region of interest of a subject subjected to a magnetic resonance imaging procedure, comprising:

(a) a tuned primary circuit comprising a primary inductor and a primary capacitor connected in series;

(b) a tuned secondary circuit comprising a secondary inductor and a secondary capacitor connected in series, said secondary inductor being proximate to and inductively non-overcoupled to said primary inductor, said primary and secondary inductors forming a spatial region for receiving the anatomical region of interest of said subject therein, said spatial region having a substantially uniform coil sensitivity therethrough, each of said primary and secondary inductors receiving said MRI signals from the anatomical region of interest of said subject; and (c) means for transmitting said MRI signals from said secondary circuit.

2. The dedicated radio frequency coil according to claim 1, wherein each of said primary and secondary inductors are symmetric about a longitudinal axis therethrough and form a substantially cylindrical shape thereabout, and wherein said primary and secondary inductors are coaxially aligned.

3. The dedicated radio frequency coil according to claim 2, wherein said primary and secondary inductors are solenoidal.

4. The dedicate radio frequency coil according to claim 2, wherein said primary inductor comprises a plurality of spiral coils electrically connected in parallel, each of said spiral coils being wound about said longitudinal axis and extending progressively radially outward from said axis.

5. The dedicated radio frequency coil according to claim 2, wherein said secondary inductor comprises a pair of loops electrically connected in parallel, and wherein the diameter of said secondary inductor is substantially equal to the diameter of said cylindrically-shaped primary inductor.

6. The dedicated radio frequency coil according to claim 1, wherein said anatomical region of interest is a head.

7. The dedicated radio frequency coil according to claim 1, wherein said anatomical region of interest is a knee.

8. A dedicated radio frequency coil for receiving MRI signals emitted from an anatomical region of interest of a subject subjected to a magnetic resonance imaging procedure, comprising:

(a) a tuned primary circuit comprising a first spiral coil and a capacitor in series, said first spiral coil being wound about a longitudinal axis and extending progressively radially therefrom;

(b) a tuned secondary circuit comprising a secondary inductor, said secondary inductor being proximate to and inductively non-overcoupled to said primary circuit, each of said primary and secondary inductors receiving said MRI signals from the anatomical region of interest of said subject; and (c) positioning means for positioning said secondary circuit relative to said primary circuit.

9. The dedicated radio frequency coil according to claim 8, wherein said secondary inductor comprises a single conductive turn.

10. The dedicated radio frequency coil according to claim 9, wherein said single conductive turn of said secondary inductor comprises a single loop of conductor and a capacitor in series, said single loop having a pair of confronting ends spaced apart and forming a gap therebetween.

11. The dedicated radio frequency coil according to claim 9, wherein said single conductive turn of said secondary inductor comprises a pair of conductive loops, each of said loops having a pair of confronting ends, and a pair of conductive links for connecting said pair of conductive loops in parallel, each link connecting a respective end of one of said loops to a corresponding end of the other loop.

12. The dedicated radio frequency coil according to claim 8, wherein said tuned primary circuit further comprises: a second spiral coil would about said longitudinal axis and extending progressively radially therefrom, and means for electrically connecting said first and second spiral coils in parallel.

13. The dedicated radio frequency coil according to claim 12, wherein said first and second spiral coils each have a central aperture therethrough about said longitudinal axis for receiving said anatomical region of interest of said subject therein, and wherein said positioning means aligns said central apertures.

14. The dedicated radio frequency coil according to claim 12, wherein said first and second spiral coils form a spatial region therebetween having a substantially uniform coil sensitivity therethrough.

15. The dedicated radio frequency coil according to claim 8, wherein said anatomical region of interest is a head.

16. The dedicated radio frequency coil according to claim 8, wherein said anatomical region of interest is a knee.

17. A method for receiving MRI signals from an anatomical region of interest of a subject, comprising the following steps:

positioning an inductively coupled radio frequency coil comprising a tuned primary circuit and a tuned secondary circuit proximate the anatomical region of interest of said subject, said primary and secondary circuits forming a spatial region surrounding the anatomical region of interest of said subject, said spatial region having a substantially uniform coil sensitivity therethrough;

irradiating the anatomical region of interest of said subject within said spatial region to excite the emission of MRI signals therefrom; and receiving the emitted MRI signals with said inductively coupled radio frequency coil.

18. The method according to claim 17, further comprising the step of changing the inductive coupling between said primary and secondary circuits before irradiating the anatomical region of interest of said subject.

19. The method according to claim 17, wherein the anatomical region of interest of said subject is irradiated by injecting radio frequency energy into one of said primary and secondary circuits.

20. The method according to claim 17, wherein the anatomical region of interest of said subject is selected from the group consisting of a head and a knee.

21. The dedicated radio frequency coil according to claim 2, wherein said secondary inductor comprises at least two coil members spaced apart from one another, and means conductively connecting said coil members in parallel.

22. The dedicated radio frequency coil according to claim 21, wherein at least one of said at least two coil members of said secondary inductor is a spiral coil, said at least one spiral coil being wound about said longitudinal axis and extending progressively radially outward from said axis.

23. The dedicated radio frequency coil according to claim 8, wherein said secondary inductor comprises at least two coil members spaced apart from one another, and means conductively connecting said coil members in parallel.

24. The dedicated radio frequency coil according to claim 23, wherein at least one of said at lest two coil members of said secondary inductor is a spiral coil, said at least one spiral coil being wound about said longitudinal axis and extending progressively radially outward from said axis.

25. The dedicated radio frequency coil according to claim 4, wherein said means conductively connecting said coil members in parallel comprises a plurality of links.

26. The dedicated radio frequency coil according to claim 1, wherein the degree of coupling is essentially critical coupling.

27. The dedicated radio frequency coil according to claim 8, wherein the degree of coupling is essentially critical coupling.

28. The dedicated radio frequency coil according to claim 2, wherein said primary inductor comprises a plurality of loops electrically connected in parallel.

29. A radio frequency coil for receiving MRI signals emitted from an anatomical region of interest of a subject subjected to a magnetic resonance imaging procedure, comprising:

(a) a tuned primary circuit comprising a primary inductor and a primary capacitor connected in series;

(b) a tuned secondary circuit comprising a secondary inductor and a secondary capacitor connected in series, said secondary inductor being proximate and inductively coupled to said primary inductor, said primary and secondary inductors forming a spatial region for receiving the anatomical region of interest of said subject therein, each of said primary and secondary inductors receiving said MRI signals from the anatomical region of interest of said subject; and (c) means for transmitting said MRI signals from said secondary circuit.

30. The radio frequency coil accordingly to claim 29, wherein each of said primary and secondary inductors are symmetric about a longitudinal axis therethrough and form a substantially cylindrical shape thereabout, and wherein said primary and secondary inductors are coaxially aligned.

31. A radio frequency coil for receiving MRI signals from an anatomical region of interest of a subject subjected to a magnetic resonance imaging procedure, comprising:

(a) a tuned primary circuit comprising a spiral coil and a capacitor in series, said spiral coil being wound about a longitudinal axis and extending progressively radially therefrom;

(b) a tuned secondary circuit comprising a secondary inductor, said secondary inductor being proximate and inductively coupled to said primary circuit, said primary and secondary inductors forming a spatial region for receiving the anatomical region of interest of said subject therein, each of said primary and secondary inductors receiving said MRI signals from the anatomical region of interest of said subject; and (c) positioning means for positioning said secondary circuit relative to said primary circuit.

32. The radio frequency coil according to claim 31, wherein said secondary inductor comprises a spiral coil wound about a longitudinal axis and extending progressively radially therefrom.

33. A radio frequency coil for receiving MRI signals from an anatomical region of interest of a subject subjected to a magnetic resonance imaging procedure, comprising:

(a) a tuned primary circuit comprising a primary inductor and a primary capacitor connected in series, said primary inductor comprising at least two coil members spaced apart from one another, and means conductively connecting said coil members in parallel;

(b) a tuned secondary circuit comprising a secondary inductor and a secondary capacitor connected in series, said secondary inductor being proximate to and inductively non-overcoupled to said primary inductor, said primary and secondary inductors forming a spatial region for receiving the anatomical region of interest of said subject therein, said spatial region having a substantially uniform coil sensitivity therethrough, each of said primary and secondary inductors receiving said MRI signals from the anatomical region of interest of said subject; and (c) means for transmitting said MRI signals from said secondary circuit.

34. The radio frequency coil according to claim 33, wherein each of said coil members is a spiral coil wound about a longitudinal axis and extending progressively radially therefrom.

35. The radio frequency coil according to claim 33, wherein said secondary inductor comprises at least two coil members spaced apart from one another, and means conductively connecting said coil members in parallel.

36. The radio frequency coil according to claim 35, wherein each of said coil members of said secondary inductor is a spiral coil wound about a longitudinal axis and extending progressively therefrom.

37. A radio frequency coil for receiving MRI signals from anatomical regions of interest of a subject subjected to a magnetic resonance imaging procedure, comprising:

(a) a tuned primary circuit comprising a primary inductor and a capacitor in series;

(b) a tuned secondary circuit comprising a secondary inductor, said secondary inductor being proximate to and approximately critically inductively coupled to said primary circuit, each of said primary and secondary inductors receiving said MRI signals from the anatomical region of interest of said subject; and (c) positioning means for positioning said secondary circuit relative to said primary circuit.

38. The radio frequency coil according to claim 37, wherein said primary inductor comprises at least two spiral coils each wound about a longitudinal axis and extending progressively radially therefrom, and means conductively connecting said at least two spiral coils in parallel.

39. The radio frequency coil according to claim 38, wherein said secondary inductor comprises at least two coil members spaced apart from one another, and means conductively connecting said coil members in parallel.

40. The radio frequency coil according to claim 39, wherein said coil members of the secondary inductor are spiral coils each wound about a longitudinal axis and extending radially therefrom.

41. A radio frequency coil for transmitting radio frequency energy to an anatomical region of interest of a subject during a magnetic resonance imaging procedure, comprising:

(a) a tuned primary circuit comprising a primary inductor and a primary capacitor connected in series, wherein the primary inductor comprises at least two conductive loops electrically connected in parallel;

(b) a tuned secondary circuit comprising a secondary inductor and a secondary capacitor connected in series, said secondary inductor being proximate to and inductively coupled to said primary inductor, said primary and secondary inductors forming a spatial region for receiving the anatomical region of interest of said subject therein; and (c) means for transmitting said MRI signals from said secondary circuit.

42. The radio frequency coil according to claim 41, wherein each primary inductor comprises a spiral coil wound about a longitudinal axis and extending progressively radially outward from said axis, said spiral coils being electrically connected in parallel.

43. The radio frequency coil according to claim 42, wherein said secondary inductor comprises at least two conductive loops electrically connected in parallel.

44. The radio frequency coil according to claim 43, wherein each of said conductive loops of said secondary inductor comprises a spiral coil wound about a longitudinal axis and extending progressively radially therefrom, said spiral coils being electrically connected in parallel.

45. The radio frequency coil according to claim 41, wherein said secondary inductor comprises at least two conductive loops electrically connected in parallel.

46. The radio frequency coil according to claim 45, wherein each of said conductive loops comprises a spiral coil wound about a longitudinal axis and extending progressively radially therefrom, said spiral coils being electrically connected in parallel.

47. The radio frequency coil according to claim 29, wherein said primary conductor comprises at least two coil members conductively connected in parallel.

48. The radio frequency coil according to claim 47, wherein the coil members of the primary inductor are each spiral coils.

49. The radio frequency coil according to claim 29, wherein said secondary inductor comprises at least two coil members conductively connected in parallel.

50. The radio frequency coil according to claim 49, wherein the coil members of the secondary inductor are each spiral coils.

* * * * *

UNITED STATES PATENT AND TRADEMARK OFFICE
CERTIFICATE OF CORRECTION

PATENT NO. : 5,583,438
DATED : December 10, 1996
INVENTOR(S) : Eydelman

It is certified that error appears in the above-indentified patent and that said Letters Patent is hereby corrected as shown below:

Column 4, line 55, after "inductor" insert --27 is a single turn loop in series with the capacitor--; line 62, "is" should read --if--.

Column 6, line 19, "dedicate" should read --dedicated--; line 66, "would" should read --wound--.

Column 7, line 58, "lest" should read --least--.

Signed and Sealed this

Twenty-second Day of April, 1997

*Attest:*

BRUCE LEHMAN

*Commissioner of Patents and Trademarks*

*Attesting Officer*